(12) United States Patent
Graf et al.

(10) Patent No.: US 9,366,720 B2
(45) Date of Patent: Jun. 14, 2016

(54) SENSOR PROTECTION

(75) Inventors: Markus Graf, Zurich (CH); Matthias Streiff, Zurich (CH); Werner Hunziker, Stafa (CH); Christoph Schanz, Stafa (CH)

(73) Assignee: Sensirion AG, Stafa (CH)

( * ) Notice: Subject to any disclaimer, the term of this patent is extended or adjusted under 35 U.S.C. 154(b) by 222 days.

(21) Appl. No.: 13/981,651

(22) PCT Filed: Jan. 26, 2012

(86) PCT No.: PCT/CH2012/000020
§ 371 (c)(1),
(2), (4) Date: Oct. 10, 2013

(87) PCT Pub. No.: WO2012/100361
PCT Pub. Date: Aug. 2, 2012

(65) Prior Publication Data
US 2014/0028340 A1  Jan. 30, 2014

(30) Foreign Application Priority Data

Jan. 27, 2011 (EP) .................................. 11000640

(51) Int. Cl.
| | |
|---|---|
| *G01R 31/00* | (2006.01) |
| *G01R 31/28* | (2006.01) |
| *B81C 1/00* | (2006.01) |
| *H01L 23/00* | (2006.01) |
| *H01L 21/00* | (2006.01) |

(Continued)

(52) U.S. Cl.
CPC ........ *G01R 31/2831* (2013.01); *B81C 1/00333* (2013.01); *H01L 24/94* (2013.01); *G01N 33/0027* (2013.01); *G09G 1/00* (2013.01); *H01L 21/00* (2013.01); *H01L 2221/00* (2013.01); *H01L 2224/13* (2013.01)

(58) Field of Classification Search
CPC ....... H01L 21/00; H01L 2221/00; G09G 1/00
See application file for complete search history.

(56) References Cited

U.S. PATENT DOCUMENTS

| | | | |
|---|---|---|---|
| 4,825,684 A | 5/1989 | Nishiguchi et al. | |
| 5,001,423 A | 3/1991 | Abrami et al. | |
| 6,083,344 A | * 7/2000 | Hanawa et al. | ............ 156/345.28 |

(Continued)

FOREIGN PATENT DOCUMENTS

| | | |
|---|---|---|
| EP | 0265816 | 5/1988 |
| EP | 0438957 | 1/1990 |

(Continued)

OTHER PUBLICATIONS

PCT International Search Report in connection with PCT/CH2012/000020, completed on Sep. 13, 2012 and mailed Sep. 21, 2012.

*Primary Examiner* — Huy Q Phan
*Assistant Examiner* — Temilade Rhodes-Vivour
(74) *Attorney, Agent, or Firm* — Cooper & Dunham LLP (57) ABSTRACT

In a method for manufacturing a sensor chip a spacer (3) is arranged at the front side (11) of a substrate (1) at which front side (11) a sensing element (2) is arranged, too. Holes (14) are etched for building vias (15) extending through the substrate (1) between the front side (11) of the substrate (1) and its back side (12). After etching, the holes (14) are filled with conductive material to complete the vias (15). The spacer (3) provides protection to the sensing element (2) and the sensing chip throughout the manufacturing process.

17 Claims, 5 Drawing Sheets

(51) Int. Cl.
  *G09G 1/00* (2006.01)
  *G01N 33/00* (2006.01)

(56) References Cited

U.S. PATENT DOCUMENTS

| | | | |
|---|---|---|---|
| 6,189,483 B1* | 2/2001 | Ishikawa et al. | 118/723 E |
| 6,479,320 B1 | 11/2002 | Gooch | |
| 6,528,875 B1 | 3/2003 | Glenn et al. | |
| 2002/0045272 A1* | 4/2002 | McDevitt et al. | 436/518 |
| 2005/0029221 A1 | 2/2005 | Chang et al. | |
| 2005/0104204 A1 | 5/2005 | Kawakubo et al. | |
| 2006/0053862 A1 | 3/2006 | Mayer et al. | |
| 2006/0131731 A1 | 6/2006 | Sato | |
| 2006/0179942 A1 | 8/2006 | Fukaura et al. | |
| 2007/0190691 A1* | 8/2007 | Humpston | B81C 1/00269 438/113 |
| 2007/0190747 A1* | 8/2007 | Humpston | B81C 1/00285 438/460 |
| 2008/0283991 A1 | 11/2008 | Reinert | |
| 2008/0315230 A1 | 12/2008 | Murayama | |
| 2009/0178751 A1* | 7/2009 | Presley | H01L 21/67225 156/60 |
| 2009/0206349 A1 | 8/2009 | Yamada et al. | |
| 2010/0284553 A1 | 11/2010 | Conti et al. | |

FOREIGN PATENT DOCUMENTS

| | | |
|---|---|---|
| EP | 0817256 | 1/1998 |
| EP | 1628132 | 2/2006 |
| EP | 2252077 | 11/2010 |
| JP | 63110671 | 5/1988 |
| JP | 9033567 | 2/1997 |
| WO | 0156920 | 8/2001 |
| WO | 2005102911 | 11/2005 |
| WO | 2008023824 | 2/2008 |

* cited by examiner

SENSOR PROTECTION

CROSS-REFERENCE TO RELATED APPLICATIONS

This application is a §371 national stage of PCT International Application No. PCT/CH2012/000020, filed Jan. 26, 2012, claiming priority of European Patent Application 11000640.0 filed on Jan. 27, 2011 the entire contents of each of which are hereby incorporated by reference into this application in its entirety.

TECHNICAL FIELD

The present invention relates to a method for manufacturing a sensor chip, and to a testing device.

BACKGROUND ART

Subject to the application, sensors tend to be integrated on semiconductor substrates. This kind of manufacturing is beneficial in that the size of the sensors can significantly be reduced compared to discrete type sensors, and such sensors can be arranged next to electronic circuitry integrated on the same semiconductor substrate which circuitry may include functions acting on a signal delivered by the sensor such as amplification, evaluation, etc.

An integrated chip comprising a sensor is called sensor chip in the following. In such sensor chip, the sensor and possibly electronic circuitry are arranged at a front side of a substrate. The circuitry may be formed by CMOS processing, and the building and/or arranging of a sensing element of the sensor on the front side may be implemented in a way compatible to CMOS processing. When such sensor chip needs to be integrated into a processing system, the sensor chip typically will be connected to circuitry residing on a different circuit board, such as a printed circuit board, for example. A preferred way for mounting a sensor chip to such circuit board is a technique called flip chip mounting in which the sensor chip is flipped such that its front side containing the sensing element and the circuitry faces the circuit board and is electrically connected to it. The electrical connection typically is achieved between contact pads arranged at the front side of the sensor chip and contact pads arranged on the circuit board and solder material in between.

However, now the sensing element faces the circuit board which may not be preferred for various reasons: In case the sensor shall detect a quantity of a measure in the environment of the sensor, such measure may not have sufficient access to the sensing element for the reason of its arrangement facing the circuit board. And even if there is sufficient access granted to the medium to be measured, it may not be appreciated that such medium also gets in touch with the circuit board. In case, for example, the medium to be measured is a gas, such gas may damage the circuitry on the circuit board.

For solving the above problem, a technique called through-silicon vias may be applied. Such vias are arranged in the semiconductor substrate and represent vertical electrical connections between the front side of the substrate and its back side. A sensor chip with through-silicon vias can be mounted on the circuit board with its back side facing the circuit board and with its front side including the sensing element facing away from the circuit board. Contact pads arranged at the back side of the sensor chip allow electrically contacting the circuit board.

However, the handling of such sensor chip appears to be difficult in that both sides of the chip, i.e. the front side and the back side contain exposed elements such as the sensing element and the contact pads.

DISCLOSURE OF THE INVENTION

The problem to be solved by the present invention is therefore to provide a method for manufacturing a sensor chip and testing devices improving the handling during processing.

This problem is solved by a method for manufacturing a sensor chip according to the features of the independent claim 1, and by testing devices according to the features of the independent claims 13 and 14.

The sensor chip comprises a substrate with a front side and a back side. A sensing element and conductors are arranged at the front side, and contact pads are arranged at the back side. Vias extending through the substrate between the front side and the back side are provided for electrically connecting the conductors to the contact pads. A spacer is arranged at the front side.

In processing a sensor chip, a substrate is provided with a front side and a back side, and a sensing element is arranged at the front side as is a spacer. Holes are etched into the substrate, and the holes are filled with a conducting material for building vias extending through the substrate between the front side and the back side.

The spacer is arranged for protecting the sensing element during manufacturing. There are various steps in the manufacturing process where it is preferred to deposit the sensor chip with its front side onto some support. This may be owed to a need for applying manufacturing steps from the back side of the substrate or to a need for electrically contacting the contact pads arranged at the back side of the substrate. In such scenarios, the sensor chip can now be flipped and be deposited onto the support by means of its spacer, such that the spacer faces and sits on the support. As a result, the sensing element is protected and does not need to get in touch with any support during which contact the sensing element may become damaged or destroyed. The spacer acts as a protection element being arranged at the front side of the substrate and may protect not only the sensing element but also other structures such as integrated circuitry arranged at the front side of the substrate.

Advantageous embodiments of the present idea are listed in the dependent claims as well as in the description below.

All the described embodiments shall similarly pertain to the testing device, its use, and to the method for manufacturing a sensor chip. Synergetic effects may arise from different combinations of the embodiments although they might not be described in detail.

Further on it shall be noted that all embodiments of the present invention concerning a method might be carried out in the order of the steps as described or in any other order unless otherwise explicitly mentioned. The disclosure and scope of the invention shall include any order of steps irrespective of the order listed in the claims.

BRIEF DESCRIPTION OF THE DRAWINGS

The embodiments defined above and further embodiments, features and advantages of the present invention can also be derived from the examples of embodiments to be described hereinafter in connection with the drawings in which the figures illustrate.

MODES FOR CARRYING OUT THE INVENTION

Figure 1A:
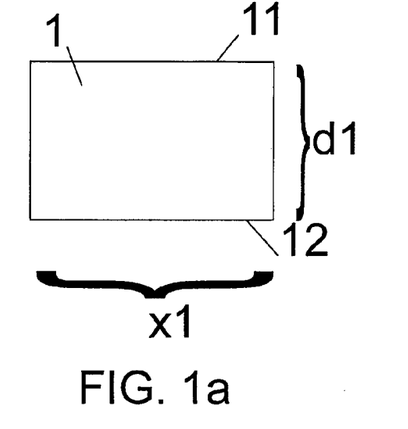
FIG. 1a-1g in a longitudinal cut each, different schematic states of a sensor chip during its manufacture according to an embodiment of the present invention, and in FIG. 1g the resulting sensor chip according to an embodiment of the present invention, and FIGS. 2a-2l in a longitudinal cut each, different schematic states of sensor chip processing on a wafer scale according to an embodiment of the present invention, and in FIG. 2l a resulting sensor chip arranged on a circuit board according to an embodiment of the present invention.
Figure 1B:
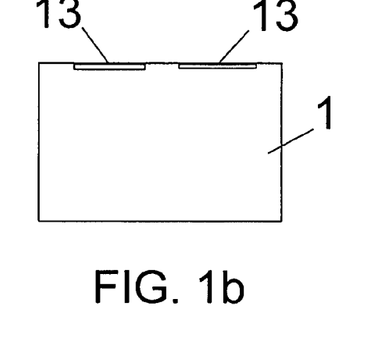
Figure 1C:
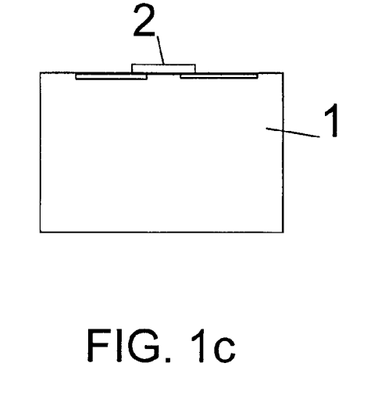
Figure 1D:
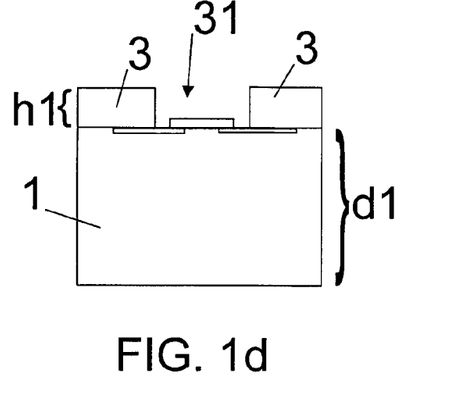
Figure 1E:
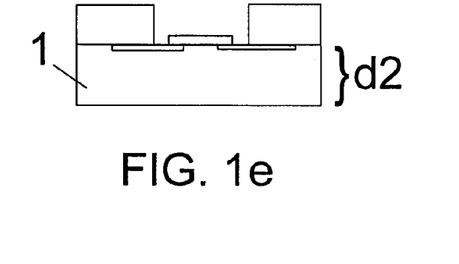
Figure 1F:
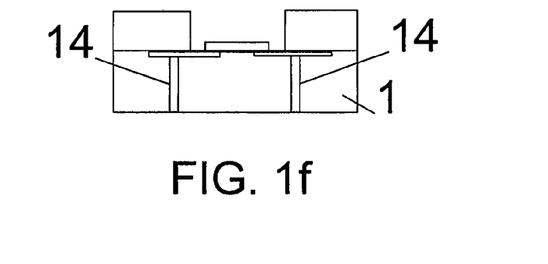
Figure 1G:
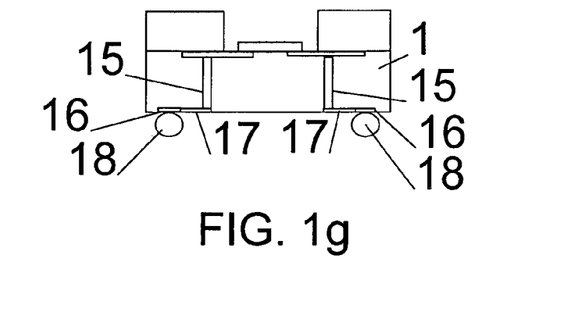

The FIGS. 1a to 1g schematically illustrate different states of a sensor chip, each in a longitudinal cut, during its manufacture according to an embodiment of the present invention. In FIG. 1g, the resulting sensor chip is shown.

According to FIG. 1a, a schematic substrate 1 is provided comprising a front side 11 and opposite to the front side 11 a back side 12. A height/depth/vertical extension/thickness of the substrate 1 is denoted by d1. In the present example, the thickness d1 of the substrate 1 is between 500 µm and 800 µm which are a common standard thicknesses of wafers. Orthogonal to the vertical extension d1 of the substrate 1, a non visible surface of the substrate 1 extends into the plane of projection, which surface, also known as chip surface, is defined by a length x1 of the substrate 1 and a non-visible width y1.

The substrate 1 advantageously is a semiconductor substrate, and preferably is a silicon substrate. However, the substrate 1 also may also be embodied as a ceramic, glass, polymer or other dielectric substrate.

According to FIG. 1b, conductors 13 are applied to the first side 11 of the substrate 1, for example, by depositing metal paths where needed. In general, the semiconductor substrate 1 is structured and processed by known processes such as CMOS processes in order to build conductors and other circuitry such as evaluation or amplification circuitry subject to the application and the scope of functionality of the sensor chip. Although there is no other passive or active circuitry shown in FIG. 1b except for the conductors 13, it is understood that such circuitry may be integrated at the front side 11 of the substrate 1 where needed. In this context, when an element is to be arranged at the front side 11 of the substrate 1, such arrangement shall encompass a deposition of such element onto the surface of the substrate 1, it also shall encompass a deposition of such element onto other layers deposited on the surface of the substrate such that the element not necessarily touches the substrate 1 itself, and it shall also encompass elements/structures which are integrated into the substrate close to the surface by means of, for example, the above mentioned semiconductor processing and as such are buried below other layers. Still such elements are arranged at the front side 11 in that they are not arranged at the back side or at lateral sides of the substrate 1.

In FIG. 1c, a sensing element 2 supporting the measurement is deposited on the substrate 1 at its front side 11. Subject to the manufacturing process applied and the material the sensing element 2 is made of, the sensing element 2 may be deposited on or buried into the substrate 1. In both variants, the sensing element 2 may advantageously be formed by means of the same underlying processing steps as the circuitry is.

In FIG. 1d, a spacer 3 is arranged at the front side 11 of the substrate 1. Arranging the spacer 3 at the substrate 1 generally may include one of the following, without limitation: The spacer 3 may be an element formed separate from the substrate 1 and may be glued, bonded or otherwise mechanically connected to the substrate 1. The spacer 3 may directly be built on the substrate 1 in form of layers deposited on the substrate 1. The spacer 3 may be formed by moulding or casting onto the substrate 1.

As an interconnect layer for fixing the spacer 3 to the substrate 1 one of solder, glassfrit or a polymer layer may be applied. As shown in FIG. 1d, the spacer 3 may exhibit a form surrounding the sensing element 2. The sensing element 2 preferably is not covered by the spacer 3 in order to allow access to the sensing element 2. The spacer 3 has a height h1, which is preferably above 100 µm, and preferably is between 150 and 250 µm.

The spacer 3 may be embodied as a resist, in particular as a dry resist, for example SU-8. Alternatively, it may be formed by a cast in a moulding process in which an insert is used for forming an opening 31 in the cast above the sensing element 2. The sensor chip is placed in a mould comprising the insert; the mould is filled with the cast material and the cast material is hardened for building the spacer 3.

The spacer 3 may also be provided in form of another substrate, for example, a silicon-on-insulator, or other semiconducting layer arrangements. The spacer 3 may be made from one of a semiconductor, silicon, silicon and a silicon-oxide coating, silicon and a solderable coating, ceramic, ceramic and a silicon-oxide coating, ceramic and a solderable coating, glass, glass and a silicon-oxide coating, glass and a solderable coating, metal, metal and a solderable coating, dielectric material and a polymer. The spacer 3 may cover and protect at least part of circuitry, and in particular metal structures, integrated into the substrate 1, however, it is preferred that the spacer 3 does not cover the sensing element 2.

In case the spacer 3 is made from a photostructurable material such as a dry resist, which first is applied to the entire front side 11 of the substrate 1 and then is exposed to visible light for patterning any structures as desired, such spacer 3 may end up as a visible light transmitting structure covering electronic circuitry arranged on or in the substrate 1. However, in case of exposure to light such electronic circuitry may be impacted in its characteristic and/or its functions. In case the spacer 3 is made from a material being transparent to visible light, it is preferred to apply another layer of opaque material on top of the spacer 3 at least in regions where electronic circuitry resides underneath on or in the substrate 1. Such opaque material which shall be intransparent to visible light and/or to ultraviolet light in one embodiment may protect the electronic circuitry on the sensor chip from any light induced transformation.

Such opaque material may especially be a mould compound applied to/on top of the spacer 3 by way of transfer-moulding. Such mould compound, also referred to as encapsulation, preferably includes epoxy material. Of course, such encapsulation is not meant to cover the sensing element 2. For such purpose, the sensor chip may be arranged in a mould with an inward facing protrusion of the mould resting on the spacer 3 and forming an access opening in the encapsulation towards the sensing element 2. The mould is filled with the encapsulation material and the encapsulation material is hardened for building the encapsulation. The mould compound may be applied to the spacer 3 after the sensor chip is placed on a circuit board such as a lead frame.

In another embodiment, the photosensitive spacer 3 may be covered by a lacquer intransparent to visible light. Such lacquer may include an epoxy resin, for example. In another embodiment, the lacquer may include polyurethane. In both embodiments, it may be preferred that a light blocking pigment may be added, such as Fe3O4, for example. Such lacquer may be applied to/on top of the spacer.

In another approach, where it is desired not to apply an additional layer or encapsulation to the spacer 3, the spacer 3 may be made from a material that is structurable by exposure to an irradiation other than in the visible spectrum, such as to x-rays, deep UV or infrared radiation, for example. An example for a material specifically being sensitive to x-rays is PMMA and to deep US is SU8, each with a filler such as carbon black to block unwanted light, and optionally a filler such silica particles to achieve mould compound like properties such as for instance matching the coefficient of thermal expansion of the cured resist with the materials present in the substrate, for example Si, SiO2, SiN, metals. Hence, such x-ray sensitive resist may be applied to the entire top side 11 of the substrate 1, and subsequently may be structured by exposure to x-rays. After having built the spacer 3 in this way, there is no need for any additional protection against exposure to visible light in form of a lacquer or an encapsulation owed to the property of the spacer material that is transparent to x-rays but intransparent to visible light and ultraviolet light at least after development and curing. Hence, the sensor device may be used as such without visible light causing damages in the electronic circuitry.

Spectral ranges may be defined according textbook knowledge. Specifically, irradiation in the infrared range may include wavelenghts from 780 nm up to 1 mm, irradiation in the visible light range may include wavelenghts from 380 nm up to 780 nm, irradiation in the ultraviolet range may include wavelengths from 1 nm to 380 nm, irradiation in the deep ultraviolet range may include wavelengths from 1 nm to 300 nm, and x-ray irradiation may include wavelengths of less than 1 nm.

In conventional CMOS processing, the building of integrated structures may be finalized by applying a dielectric layer such as an oxide, a silicon oxide or a nitride layer to the substrate 1 which shall cover any metal structures such as connectors or pads on the front side 11 of the substrate 1. In view of the spacer 3 being applied to the front side 11 of the substrate 1 such dielectric layer may be omitted during manufacture of the sensor chip.

In the present example, vias reaching through the substrate are preferably processed in subsequent steps. Such vias are manufactured by first etching holes into the substrate and filling these holes with electrically conductive material. For the reason that a high aspect ratio needs to be achieved for these holes conventional etching techniques may not be applicable. Special etching techniques such as anisotropic etching, which includes, for example deep reactive-ion etching (DRIE), may be applied for etching holes with such high aspect ratio. On the other hand, in such special etching techniques a diameter of the etched hole may strongly depend on its depth which depth may be equivalent to the thickness of the substrate. Approximately, the diameter evoked may be half of the depth of the hole. Silicon wafers from which the substrate for integrated circuits is formed typically exhibit a thickness of several hundred micrometers μm, for example 780 μm. Given this thickness, the diameter of a hole etched through the entire substrate for building a through-silicon via is about 390 μm. On the other hand, and again subject to the application, sensing elements may only cover small areas of a semiconductor chip such that even with additional circuitry included in such chip the overall chip surface may not exceed the order of few mm². It becomes apparent that a couple of silicon through vias would claim a major part of the surface of such a chip. As a result, the chip surface would need to be extended only because of the vias representing the largest structures on the chip. However, it is not preferred that any achievement in scaling down the sensing element and the circuitry is eaten up by the vias. As a result, it is preferred that prior to etching holes into the substrate 1, the thickness d1 of the substrate 1 may be reduced in order to achieve holes with a diameter smaller than the diameter of holes etched into a substrate/wafer having a standard thickness.

In the step represented by FIG. 1e, the substrate 1 is thinned, e.g. by grinding, to a reduced thickness d2 less than 300 μm, preferably less than 100 μm, and in a very preferred embodiment less than 50 μm. This means, that material from the substrate 1 is removed for reducing the thickness d1 of the substrate 1 down to the reduced thickness d2 in order to allow etching small size/diameter holes for realizing vias, a diameter of which holes depends on the thickness of the substrate 1. For example, by using an anisotropic etching technique for building holes reaching through the substrate 1 of 150 μm thickness the diameter of such holes may be in the order of 75 μm. In case the substrate 1 may be thinned down to at least 50 μm, isotropic etching techniques may also be applied instead. As a result, multiple holes 14 for vias 15 can be etched into the substrate 1 after the substrate 1 has been thinned to the reduced thickness d2 without claiming the entire space on the chip surface. For many sensor applications, at least four through-silicon vias are formed, two for power, and two for communication.

The functionality of the spacer 3 may now be two fold: First, for thinning the substrate 1 the present sensor chip may need to be flipped and sit on a support. In such position, with the spacer 3 facing the support the sensing element 2 is protected by the spacer 3 in that the sensing element 2 does not get in touch with the support. And second, the spacer 3 may additionally act as a stiffener to the present sensor chip for the reason that as a result of the thinning step the thickness of the substrate 1 may be reduced to levels at which the substrate 1 no longer forms a rigid element but rather represents a thin flexible element. In order to compensate for the flexibility achieved as a by-product of the efforts of reducing the diameter of the through vias, the spacer 3 allows the sensor chip to form a rather rigid structure again and improves mechanical stability of the sensor chip and its handling.

A state of the sensor chip after etching holes 14 into the substrate 1 is shown in FIG. 1f. The holes 14 preferably are etched into the substrate 1 from its back side 12. In a final step, the holes 14 are filled with conducting material such as Cu, polySi, Si, or others for implementing the various vias 15. In this context, a via 15 is understood as a conducting element reaching through the substrate 1. Conductors 17 provided at the back side 12 of the substrate 1 may connect the vias 15 to contact pads 16 provided elsewhere on the back side 12 of the substrate 1. In this respect, the back side 12 of the substrate 1 may be understood as a redistribution layer which allows for finally arranging solder balls 18 on the contact pads 16 with a sufficient distance from each other, such as shown in FIG. 1g.

The conductors 17 of such redistribution layer may be formed on the substrate 1 at the very beginning of the process, for example, after the step illustrated in FIG. 1b. In another embodiment, where feasible in terms of space, some or all ends of the vias 15 at the back side 12 of the substrate 1 may form or especially be formed as contact pads 16. During etching and filling the holes 14, the sensor chip may be flipped and be seated on its spacer 3 which again protects the sensing element 2 and the other integrated structures during manufacturing. As a result, no other carrier is needed during building the through-silicon vias 15.

For the present embodiment of a manufacturing process it is advantageous that the material used for the spacer 3 may show a high temperature stability and may be insensitive to treatments used during building the through-silicon vias 15 for the reason that the spacer 3 may be exposed to high temperatures and such treatments during building the through-silicon vias 15.

In an advantageous embodiment, the spacer 3 may comprise a membrane being arranged distant from the sensing element 2 for covering the opening 31. An example of such membrane 51 is shown in FIG. 2e. Such membrane 51 may be a polymer layer, be bonded to the spacer 3, and be provided as temporary protection during manufacturing, or, alternatively, as a permanent cover provided it allows sufficient access to the sensing element 2.

The sensor chip according to FIG. 1g represents a sensor chip resulting from the previous manufacturing steps. Such sensor chip can now be mounted to a circuit board with its back side 11 facing the circuit board. For such mounting, the sensor chip may be pressed with its solder bumps 18 against the circuit board, which in one embodiment may be a printed circuit board, in order to establish an electrical connection between the contact pads 16 of the sensor chip and contact pads of the circuit board. The solder bumps 18 may be hardened or otherwise treated such that a reliable electrical connection is established. In addition, the sensor chip may be mechanically fixed to the circuit board, for example by means of an adhesive at the back side 12 of the sensor chip, or by other means.

As a result, the front side 11 of the sensor chip, and in particular its sensing element 2, faces the environment. In such arrangement, the circuit board can be shielded from the measuring environment, for instance by means of an additional housing which may be sealed against the spacer 3. The spacer continues to provide protection to the sensing element 2 also during operation of the sensor chip. At the same time, the sensing element 2 is sufficiently exposed to the measurement environment. There are no elements preventing access to the sensing element 2 as are when the sensor chip would be flip chip mounted to the circuit board. Any sensor signal from the sensing element or signals derived from such sensor signal now can be transmitted to the circuitry on the circuit board via the connectors 13 and the vias 15.

As such, the vias 15 represent an electrical connection between the front side 11 of the substrate 1 and its back side 12 and in particular may help to connect conductors 13 at the front side 11 of the substrate 1 with contact pads 16 on its back side. The sensor element 2 may be directly connected to the conductors 13 or via other circuitry. In case the substrate 1 is embodied as a silicon substrate, the vias 15 may be named through-silicon vias.

The present order of manufacturing steps is advantageous in view of different aspects: In the first steps according to the FIGS. 1a to 1c, standard semiconductor chip manufacturing processes may be applied. As mentioned above, the spacer 3 may be applied as protector during manufacturing of the vias 15. However, the spacer 3 may already perform a protecting function earlier in the process during a possible thinning of the substrate 1. In this context, it is beneficial that the spacer 3 is already attached to the substrate 1 prior to thinning the substrate 1 to its reduced thickness d2.

Still, any manufacturing steps may take a different order than listed in the claims. For example, the sensing element 2 may be arranged at the substrate 1 after the spacer 3 has been arranged at the substrate 1 provided that the technology for arranging the sensing element 2 is not prevented by the already arranged spacer 3. Provided handling allows, the spacer 3 may be arranged at the substrate 1 only for processing steps such as testing the sensor chip as will be explained in more detail with respect to FIG. 2. Provided handling allows, the vias 15 may be built first, and the circuitry/conductors 13 and the sensing element 2 may also be formed in a later step.

In another embodiment of manufacturing a sensor chip, the circuitry and the sensitive element 2 are integrated into the substrate 1 at the very beginning according to FIGS. 1a to 1c. In a next step, the thickness d1 of the substrate 1 is reduced, for example by means of thinning its back side 12 according to FIG. 1e, however, without the spacer 3 already being applied. In a next step, the through-silicon vias 15 are built according to FIGS. 1f and 1g, again without the spacer 3 being applied to the substrate 1. After having formed the through-silicon vias 15 in the substrate 1, the spacer 3 is arranged according to FIG. 1d, and solder bumps 18 are attached to the contact pads 16 such that a sensor chip according to FIG. 1g is produced. Such processing is advantageous if the material used for the spacer 3 may show only low temperature stability and/or sensitivity to treatments used during forming the through-silicon vias 15. However, it may be preferred that during the processing of the through-silicon vias 15 a carrier may be applied for supporting the thinned substrate 1 and protecting it from being damaged.

Figure 2A:
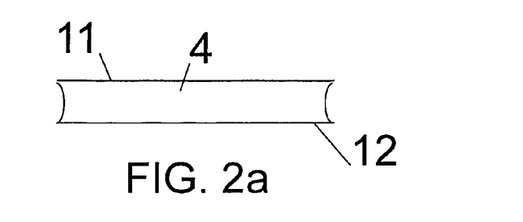
Figure 2B:
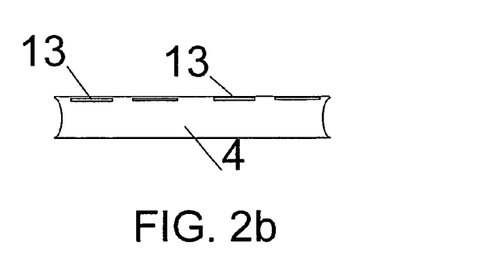
Figure 2C:
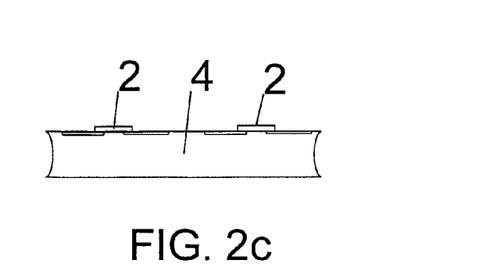
Figure 2D:
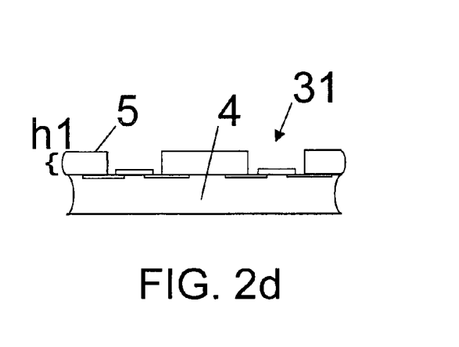
Figure 2E:
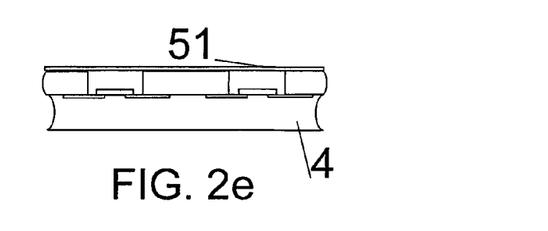
Figure 2F:
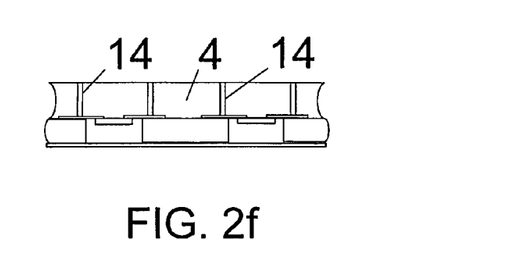
Figure 2G:
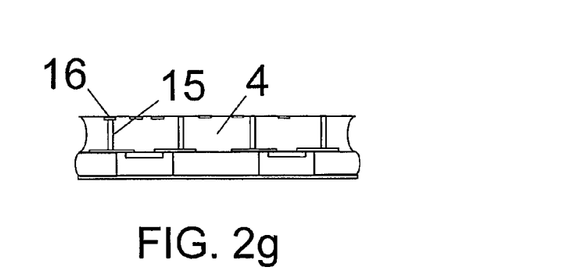
Figure 2H:
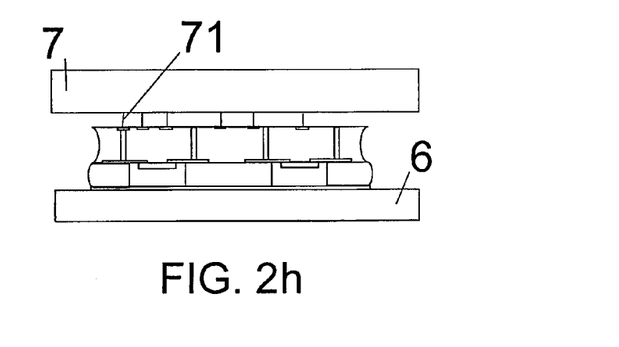
Figure 2I:
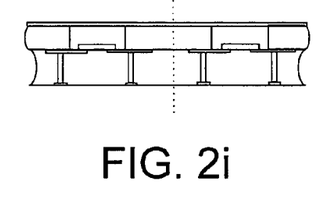
Figure 2K:
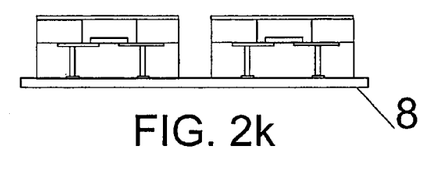
Figure 2L:
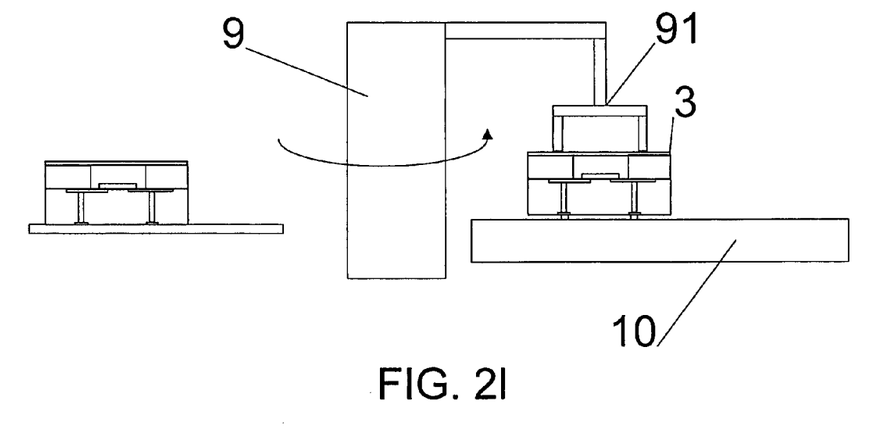

FIGS. 2a-2l schematically show different states of sensor chip processing on wafer scale, in a longitudinal cut each, according to an embodiment of the present invention. In FIG. 2l a resulting sensor chip arranged on a circuit board is illustrated according to an embodiment of the present invention.

In FIG. 2a, instead of a single substrate from which an individual sensor chip may be built, an entire wafer 4 is provided which wafer 4 constitutes a substrate for multiple sensor chips to be built from. In the present example, the sensor chips are separated from each other into individual elements at the very end of the manufacturing process, as will be explained later. During the entire processing the wafer 4 forms a common substrate for all the sensor chips to be built. Other than that and except for the omitted thinning step—may it be for the reason that the wafer 4 already is prepared to the required thickness or that the wafer 4 can be used in its original thickness, the initial manufacturing steps are the same as illustrated in FIG. 1.

The wafer 4 is provided with a front side 11, a back side 12, and a height/depth/vertical extension/thickness d1. A length of the wafer 4 and also its width, of course, exceed the length x1 and the width y1 of the individual substrate 1 as used according to FIG. 1a. Circuitry including conductors 13 and possibly other electronic components are integrated into the wafer 4 by means of CMOS processing, see FIG. 2b, now for multiple sensor chips to be built. In the step illustrated in FIG. 2c, an array of sensing elements 2 is formed on or in the wafer 4. Again, such sensing elements 2 can be built by the same processing steps the circuitry is built from, and, for example, such sensing elements 2 may include polymer layers receptive to humidity in the present example such that the sensor chip represents a humidity sensor for measuring a relative humidity of the environment.

The sensing elements 2 may alternatively be deposited on the wafer 4 in form of a film covering the entire wafer and be structured to finally form the individual sensing elements 2 as shown in FIG. 2c.

Corresponding to the step shown in FIG. 1d, the spacers are applied to the substrate 1 subsequently. Applying/arranging the spacers 3 to/at the wafer 4 may include providing multiple spacers 3 in form of a plate 5. A shown in FIG. 2d, such plate 5 may be a plate 5 of a dry resist, for example, or other suitable material where openings 31 for accessing the sensing elements 2 are already prefabricated, or where subsequent to applying the plate 2 to the front side 11 of the wafer 4 such openings 31 are fabricated. In this context, it may be beneficial that the entire plate 5 has a length and width equivalent to the length and width of the wafer 4. The plate 5 specifically may be made from one of silicon, silicon and a silicon-oxide coating, silicon and a solderable coating, ceramic, ceramic and a silicon-oxide coating, ceramic and a solderable coating, glass, glass and a silicon-oxide coating, glass and a solderable coating, metal, metal and a solderable coating, and a polymer. Alternatively, applying/arranging the spacers 3 to/at the wafer 4 may include building multiple spacers 3 in form of layers deposited on the wafer 4. Alternatively, applying/arranging the spacers 3 to/at the wafer 4 may include building multiple spacers 3 by moulding or casting material onto the wafer 4. For this purpose, the wafer 4 is placed in a mould comprising inserts for building access openings to the sensing elements 2. The mould is filled with the cast material and the cast material is hardened for building a cast.

Again, in another embodiment, in case the spacers 3 are made from a photostructurable material such as a dry resist, it is preferred to apply another layer of opaque material on top of the spacers 3. Such opaque material which shall be intransparent to visible light may protect the electronic circuitries in the wafer 4 from any light induced transformation. Applying such layer may preferably be performed prior to cutting the wafer into individual sensor chips.

Such opaque material may especially be a mould compound applied to/on top of the spacers 3 by way of transfer-moulding. Such mould compound, also referred to as encapsulation, preferably includes epoxy resin. The wafer 4 may be arranged in a mould with inward facing protrusions of the mould resting on the spacers 3 and forming access openings in the encapsulation towards the sensing elements 2. The mould is filled with the encapsulation material and the encapsulation material is hardened for building the encapsulation. Such encapsulation not necessarily needs to encapsulate the entire chip but may only represent a layer of mould compound arranged on the spacers 3.

In another embodiment, the photosensitive spacers 3 may be covered by a lacquer intransparent to visible light. Such lacquer may include an epoxy resin, for example. In another embodiment, the lacquer may include polyurethane. In both embodiments, it may be preferred that a light blocking pigment may be added, such as Fe3O4, for example. Such lacquer may be applied to/on top of the entirety of spacers 3 prior to cutting the wafer 4 into individual sensor chips. A deposition of the lacquer may be performed immediately after the spacers 3 are built. Or, the lacquer may be applied to the spacers 3 at any time after the spacers 3 are built allowing any other manufacturing steps in between. The lacquer may be applied even after separating the sensor chips from the wafer 4.

In another approach, the spacers 3 may be made from a material that is structurable by exposure to an irradiation other than in the visible spectrum, such as to x-rays, deep UV or infrared radiation, for example. An example for a material specifically being sensitive to x-rays is PMMA, and to deep UV is SU8, each with a filler such as carbon black to block unwanted light, and optionally a filler such silica particles to achieve mould compound like properties such as for instance matching the coefficient of thermal expansion of the cured resist with the materials present in the substrate, for example Si, SiO2, SiN, metals. Hence, such x-ray sensitive resist may be applied to the entire top side 11 of the wafer 4, which resist may subsequently be structured by an exposure to x-rays.

According to FIG. 2e, a membrane layer 51 is deposited on the spacer plate 5/the spacers 3, for example by bonding, and forms part of the final spacers 3. The membrane layer 51, which may be embodied as a polymer layer, covers the openings 31, protects the sensing elements 2, is arranged distant from the sensing elements 2, and provides sufficient access for the medium to be measured. In the step represented by FIG. 2f, from the back side 12 of the wafer 4 the holes 14 are etched for all the sensor chips, advantageously by deep reactive-ion etching. For this reason, the wafer arrangement is flipped and sits by means of its membrane layer 51 on a support not shown. In the step corresponding to FIG. 2g, all the holes 14 are filled with conductive material in order to build vias 15 reaching through the entire reduced thickness d2 of the wafer 4 in order to connect the conductors 13 of each sensor chip to its contact pads 16 on the back side 12, again, which contact pads 16 may be arranged offset from the associated via 15 as shown in FIG. 2g, or may be arranged in a line the associated vias 15 at the backside 12 of the wafer 4, or may be arranged in any mix of a contact pads arrangement.

In a subsequent step of processing the sensor chips, the wafer arrangement remains in its flipped state and is seated onto a chuck 6 with its membrane layer 51 facing the chuck 6 for the purpose of testing the sensor chips, see FIG. 2h. In both scenarios, electrical connections are established to the contact pads 16 now being easily accessible. A probe head 7 comprising electrodes 71 is arranged on top of the back side 12 of the wafer 4 and the electrodes 71 are brought into contact with the contact pads 16. Now, test routines may be executed, wherein the sensing elements 2 are protected by the spacers which avoid the sensing elements 2 being in direct contact with the chuck 6.

Advantageously, during test the wafer arrangement may be exposed to a medium evoking sensor responses that can be measured by means of the electrodes 71. For example, in case the sensor chips are implemented as humidity sensors, then, humid air may be supplied to the sensing elements 2 on the wafer 4. In the arrangement according to FIG. 2h such medium advantageously is guided through openings in the chuck 6—which are not explicitly shown in FIG. 2h—for accessing the sensing elements 2 facing the chuck 6.

According to FIG. 2i, the wafer 4 may be cut, for example along the dotted line, in order to separate the sensor chips from each other. The resulting individual sensor chips may be arranged on a foil 8, and possibly glued thereto for transporting purposes only. Prior to separating the individual sensor chips, solder bumps may be applied to some or all the contact pads 16 on the back side 12 of the wafer 4 in order to prepare a mounting of the individual sensor chips to their destinations such as circuit boards.

Such foil 8 with multiple sensor chips thereon may be supplied to an automatic assembly 9 as schematically illustrated in FIG. 2l. A picker 91 picks an individual sensor chip at its spacer 3 and places such sensor chip onto its final destination which in the present example is a circuit board 10. During the assembly/packaging process, the sensing element 2 as well as the entire sensor chip is protected by means of the spacer 3 which acts as a preferred contact surface for the picker 91.

Accordingly, the sensor chip is mounted with its back side onto the circuit board 10 whereas its front side including the sensing element 2 and the spacer 3 are directed away from the circuit board 10.

Any aspect with respect to the order of manufacturing steps explained in connection with an individual sensor chip according to FIG. 1 holds for the wafer level manufacturing according to FIG. 2, too. Any such variants introduced before may be introduced with respect to the wafer level manufacturing, too. In other variants, after each of the manufacturing steps on the wafer level, it may be switched to subsequent manufacturing on the individual sensor chip level by cutting the wafer 4 and any other overlapping structures.

In preferred embodiments, the sensor chip is used as one of a humidity sensor, a liquid flow sensor, a gas flow sensor, a pressure sensor, an infrared sensor and a chemical sensor. Corresponding sensing elements are provided for each of the applications.

Figure 3:
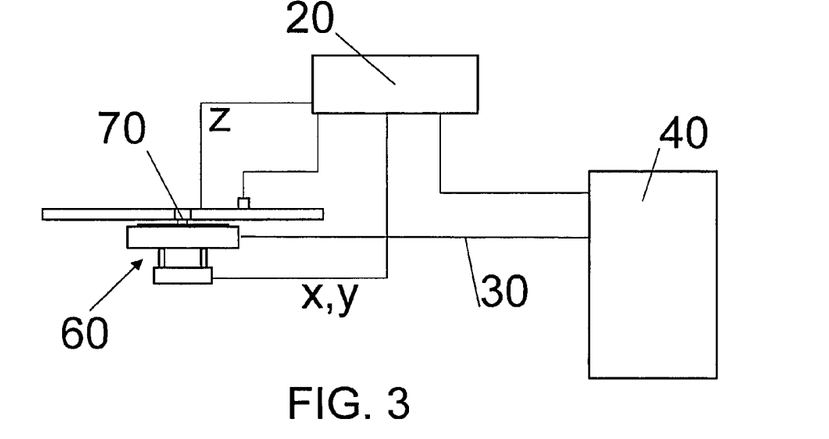
FIG. 3 a schematic set-up of a testing arrangement for testing sensor chips arranged on a wafer, according to an embodiment of the present invention, FIG. 4 a detailed view of the testing device of FIG. 3 in a lateral cut, according to an embodiment of the present invention, FIG. 5 a lateral cut of a chuck of a test device with a wafer arranged on a top surface of the chuck, according to an embodiment of the present invention.

FIG. 3 shows a schematic set-up of a testing arrangement for testing sensor chips arranged on a wafer such as shown in FIG. 2h which testing may especially include calibrating sensors. The arrangement comprises a control unit 20. The control unit 20 controls the operation of x-, y- and z-actuators of a testing device 60 adapted to contact each individual sensor chip on a wafer by means of a probe head 70. The control unit 20 further contains circuitry and software for operating the sensor chips contacted by the probe head 70 and for calibrating the same, e.g. by storing calibration data on a memory device integrated with each sensor chip. The control unit 20 also may control the operation of a fluid generator 40 producing, for example, gas for testing the sensor chips in case the sensor chips are sensitive to such gas.

Figure 4:
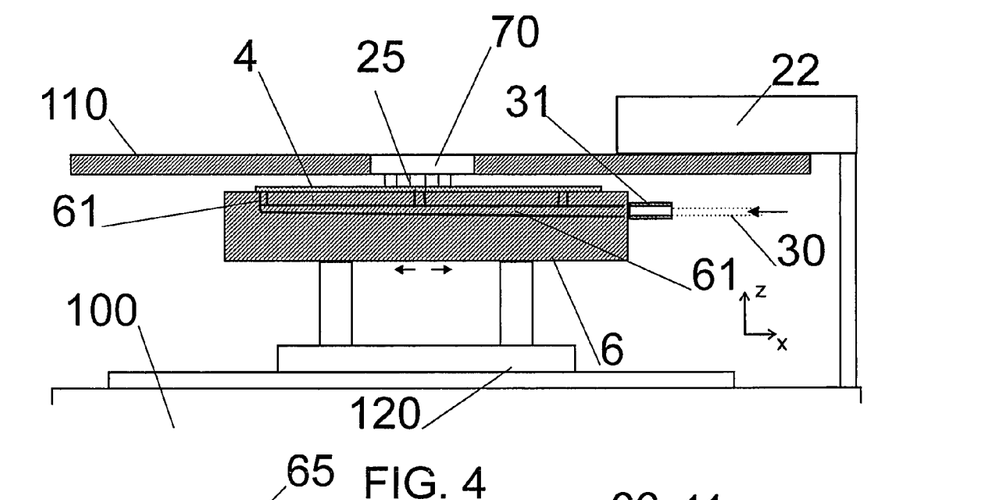

FIG. 4 illustrates a more detailed view of the testing device 60 of FIG. 3 in a lateral cut. The testing device comprises a stationary frame or stand 100 carrying an x-y-positioning device 120. The x-y-positioning device 120 carries a substantially cylindrical chuck 6 acting as a support for a wafer 4 and is enabled to accurately position the same along horizontal directions x and y. Direction x is illustrated by an arrow in the FIG. 4 while direction y is perpendicular to the plane of projection. The wafer 4 contains a two-dimensional matrix of sensors/sensor chips that are basically ready for operation but that still need to be calibrated, cut and, where applicable, packaged. The wafer 4 rests on a flat top surface of the chuck 6. A lid 110 for carrying the probe head 70 and the chuck 6 may be mutually displaceable along the z-direction for slightly separating the two parts while the x-y-positioning device 120 may move the chuck 6. A z-positioning device 22 may be arranged stationary on the frame or stand 100. The probe head 70 comprises a carrier plate mounted to the lid 110 with probe electrodes 25 mounted at the bottom side thereof. The probe electrodes 25 are arranged such that their tips can contact the contact pads of one or more sensor chips on the backside of the wafer 4. The lid 110—which in some instances may also be denoted as cover—may be heated and/or cooled for adapting a temperature of the lid 110 to a temperature of the chuck 6 which improves measurement.

For calibrating the sensor chips with the testing device of FIGS. 3 and 4, the wafer 4 comprising a plurality of sensor chips to be calibrated is placed on the chuck 6, either manually or automatically, with its spacers facing the chuck 6. The gas generator 40 is activated to generate a gas/medium with a known composition, humidity level, etc. subject to the nature of the sensor chips. A pump (not shown) in the gas generator 40 then may supply the gas through a tube 30, from which it enters the chuck 31 at one of its side walls through an inlet 31. Within the chuck 6, the gas is supplied by ducts 61, only a couple of which are schematically illustrated. The ducts 61 may represent openings in the chuck 6 and may terminate at the top surface of the chuck 6 as shown in FIG. 4 such that the medium may meet the sensing elements. Hence, the gas supplied through the ducts 61 will meet the wafer 4 at its front side 11 and as a result will meet the sensing elements 2 on the wafer 4 facing the chuck 6.

While the wafer 4 is exposed to the calibration gas, the sensor chips in the wafer 4 can be calibrated by laterally displacing the chuck 6 and by contacting each one of the sensor chips by means of the electrodes 25 of the probe head 70. Preferably, multiple sensor chips may be contacted by the electrodes 25 in parallel and as such may be tested in parallel. The calibration may include a calibration measurement and a subsequent storage of calibration data in the subject sensor chip. Preferably, the calibration data is stored in the sensor chip immediately after calibration of such chip. During calibration, the general functionality of each sensor can be tested as well, and non-functional sensors can be discarded after having cut wafer 4 later on into the individual sensor chips.

Once the calibration of the sensors on the wafer 4 is complete, the wafer 4 can be removed from the testing device 60, either manually or automatically. It then can be cut for separating the individual sensor chips.

Figure 5:
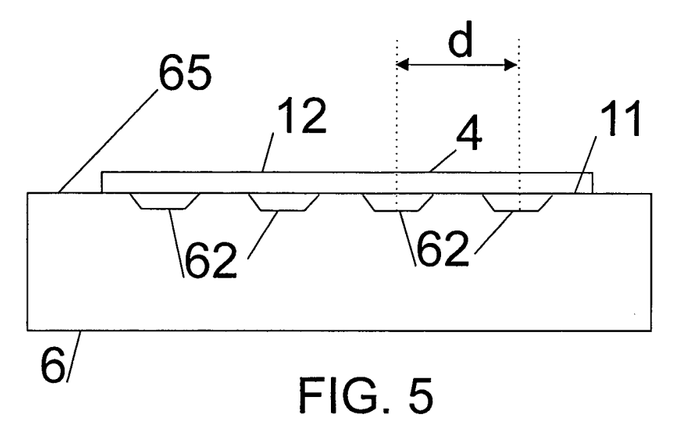

FIG. 5 shows a lateral cut of a chuck 6 of a testing device with a wafer 4 arranged on a top surface 65 of the chuck 6, such as used in an embodiment of the present invention. The present chuck 6 comprises openings in form of recesses 62 in the top surface 65 of the chuck 6. Those recesses 62 may extend through the top surface 65 of the chuck 6, preferably from one side of the chuck 6 to an opposite side of the chuck 6, wherein the recesses 62 are arranged in parallel. The cross section of the recesses 62 may vary from the one shown. Those recesses 62 are closed from the top by the wafer 4 such that channels are formed during testing, which channels are supposed to be filled with a fluid medium such as a liquid or a gas during a testing routine, and in particular during a calibration routine. The wafer 4 is not cut yet and comprises multiple sensor chips integrated in the wafer 4. Preferably, the top side 11 of the wafer 4 faces the top surface 65 of the chuck 6 such that all the sensor elements on the wafer 4 are arranged above the recesses 62 and as such become exposed to any fluid in the recesses 62. A distance d between the recesses 62 preferably corresponds to a distance between neighboring sensing elements on the wafer 4. Hence, the wafer 4 is arranged on the chuck 6 such that it rests with its spacers on the chuck 6 wherein access openings to the sensing elements are arranged over the recesses 62.

The medium for testing the subject sensor chips is supplied either directly into the recesses 62 from the sides of the chuck 6, or is supplied via ducts through the chuck 6 such as shown in FIG. 4 wherein a medium supply which is understood as the supply external to the chuck 6, such as the combination of the gas generator 40 and the pipe 30, is connected to the inlet 31 of the chuck 6 arranged in one of its side walls. In another embodiment, the openings in the chuck 6 may not comprises lateral recesses on the top surface 65 of the chuck 6 but may comprise vertical ducts within the chuck 6 wherein each sensing element is supplied with the fluid from its own duct.

Figure 6:
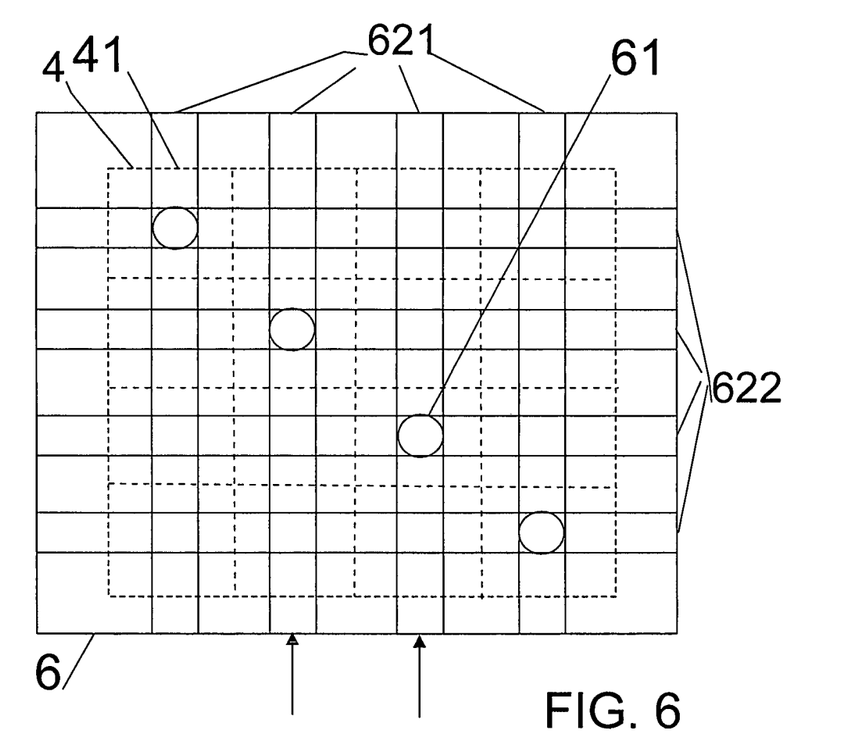
FIG. 6 illustrates a top view of a sample chuck 6 of a test device, according to an embodiment of the present invention, and FIG. 7 a lateral cut of a chuck of a test device with a wafer arranged on a top surface of the chuck, according to another embodiment of the present invention.

FIG. 6 illustrates a top view of a sample chuck 6 comprising some recesses 621 arranged in parallel to each other, and in particular in parallel at a distance corresponding to a distance between two rows of sensor chips on the wafer 4, while others of the recesses 622 are arranged orthogonal to the some recesses 621 for building a recess grid. The present embodiment may provide a more homogenous supply of the medium to the sensing elements. Again, the medium to be supplied into the recesses 621, 622 may be supplied via selected medium supplies connected laterally to some or all of the recesses such as indicated by arrows in the Figure. In a different embodiment, each recess may be connected to at least one assigned duct 61 extending into the plane of projection in FIG. 6. The wafer 4 arranged on top of the chuck 6 is illustrated by a dashed rectangle while the individual sensor chip in the wafer 4 are illustrated is by smaller rectangles 41.

It is noted, that the number of openings, including recesses and ducts as shown in FIGS. 5 and 6 are for illustration purposes only whereas a real number of openings may considerably deviate. Also the geometric layout of the recesses and/or the ducts may vary. There may also be one recess 62 supplying multiple sensing elements other than those of a common row.

Figure 7:
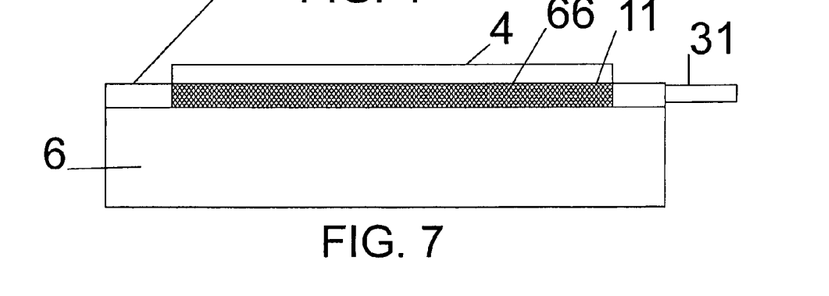

FIG. 7 shows a lateral cut of a chuck 6 of a test device with a wafer 4 arranged on a top surface 65 of the chuck 6, such as used in another embodiment of the present invention. Here, the chuck 6 does not comprise openings in form of recesses 62 in the top surface 65 of the chuck 6. Instead openings are provided in form of structures in a micro-scale such as provided by a porous material. Micro-scale in this context may allow structures up to a diameter of 1000 μm. Hence, a top layer of the chuck 6 may be embodied as a porous material layer 66 which layer may resemble a sponge in its structure. Still, the inlet 31 of the chuck 6 may be arranged at one of the side walls of the chuck 6 such that the gas may directly diffuse into the porous material layer 66, or it may be supplied elsewhere into the chuck 6 and may be supplied to the porous material layer 66 by means of ducts 61 within the chuck 6. Such porous material layer 66 may be deposited as a separate layer on the chuck 6 or may be integrated in the chuck 6 and form a single piece of material with the chuck 6. In this embodiment, the top surface 65 of the chuck 6 may preferably be treated chemically for generating pores.

While there are shown and described presently preferred embodiments of the invention, it is to be distinctly understood that the invention is not limited thereto but may be otherwise variously embodied and practiced within the scope of the following claims.

For example, the method and the testing device may not only be applied to the testing of humidity or chemical sensors, but may also be applied for testing pressure sensors containing through silicon vias.

The invention claimed is:

1. Method for manufacturing a sensor chip, comprising the steps of
    providing a substrate with a front side and a back side,
    arranging a sensing element at the front side,
    arranging a spacer at the front side,
    etching holes into the substrate, and
    filling the holes with a conducting material for building vias extending through the substrate between the front side and the back side,
    wherein the sensor chip is arranged on a chuck with the spacer facing the chuck for electrically contacting contact pads arranged at the back side with electrodes,
    wherein the substrate is provided in form of a wafer for building multiple sensor chips from, and
    wherein sensing elements and conductors for multiple sensor chips are arranged at the front side of the wafer,
    wherein multiple spacers for multiple sensor chips are arranged at the front side of the wafer,
    wherein the step of etching holes through the wafer and filling the holes for building vias for multiple sensor chips is applied prior to or after the spacers are arranged at the wafer, and
    wherein the previous four steps are implemented prior to separating the wafer into multiple sensor chips.

2. Method according to claim 1, wherein the sensor chip is tested while being arranged on the chuck.

3. Method according to claim 1, wherein the wafer is seated onto the chuck with its spacers, facing the chuck for the purpose of testing the sensor chips.

4. Method according to claim 1 wherein a probe head comprising electrodes is arranged on top of the back side of the wafer and the electrodes are brought into contact with the contact pads.

5. Method according to claim 1, wherein test routines are executed while the sensing elements being protected by the spacers thereby avoiding the sensing elements being in direct contact with the chuck.

6. Method according to claim 1, wherein during testing the wafer is exposed to a medium evoking sensor responses that can be measured by means of the electrodes.

7. Method according to claim 6, wherein the sensor chips are implemented as humidity sensors, and wherein humid air is supplied to the sensing elements on the wafer.

8. Method according to claim 6, wherein the medium is guided through openings in the chuck for accessing the sensing elements facing the chuck.

9. Method according to claim 8, wherein the openings include recesses in a top surface of the chuck, and in particular wherein at least some of the recesses in the top surface of the chuck are arranged in parallel, and in particular are arranged in parallel at a distance corresponding to a distance between two rows of sensor chips on the wafer.

10. Testing device for testing sensor chips provided in form of a wafer, the wafer comprising a front side and a back side, wherein sensing elements and conductors for the multiple sensor chips are arranged at the front side, wherein contact pads are arranged at the back side, wherein vias extend through the wafer between the front side and the back side for electrically connecting the conductors to the contact pads, and wherein spacers are arranged at the front side for protecting the sensing elements, the testing device comprising
    a chuck for arranging the wafer on with the spacers facing the chuck for electrically contacting the contact pads arranged at the back side with electrodes, comprising openings in the chuck for guiding a medium through for accessing the one or more sensing elements facing the chuck wherein the openings include recesses in a top surface of the chuck.

11. Testing device according to claim 10, wherein the openings include ducts in the chuck for connecting the recesses to a medium supply.

12. Testing device according to claim 11, wherein at least some of the recesses in the top surface of the chuck are arranged in parallel, and in particular are arranged in parallel at a distance corresponding to a distance between two rows of sensor chips on the wafer.

13. Testing device according to claim 12, wherein others of the recesses are arranged orthogonal to the at least some of the recesses for building a recess grid.

14. Testing device according to claim 10, comprising a medium supply for supplying the medium during testing for exposing the sensor chip or sensor chips to the medium for evoking sensor responses that can be measured by means of the electrodes.

15. Testing device according to claim 14, wherein the medium supply is connected to one or more of the recesses of the chuck.

16. Testing device according to claim 14, wherein the medium supply is connected to an inlet of the chuck arranged in a side wall of the chuck.

17. Testing device according to claim 14, comprising a probe head comprising electrodes, the probe head being arranged on top of the back side of the wafer when being arranged on the chuck and the electrodes being brought into contact with the contact pads of the wafer.

* * * * *